(12) United States Patent
Sweeney

(10) Patent No.: US 7,269,578 B2
(45) Date of Patent: Sep. 11, 2007

(54) SYSTEMS AND METHODS FOR DEIDENTIFYING ENTRIES IN A DATA SOURCE

(76) Inventor: Latanya Sweeney, 1420 Centre Ave., #1206, Pittsburgh, PA (US) 15219

( * ) Notice: Subject to any disclaimer, the term of this patent is extended or adjusted under 35 U.S.C. 154(b) by 795 days.

(21) Appl. No.: 10/119,553

(22) Filed: Apr. 10, 2002

(65) Prior Publication Data

US 2002/0169793 A1 Nov. 14, 2002

Related U.S. Application Data

(60) Provisional application No. 60/282,708, filed on Apr. 10, 2001.

(51) Int. Cl.
*G06Q 99/00* (2006.01)
(52) U.S. Cl. .......................................... 705/74; 705/64
(58) Field of Classification Search ................. 705/74, 705/64
See application file for complete search history.

(56) References Cited

U.S. PATENT DOCUMENTS

| | | | |
|---|---|---|---|
| 5,708,828 A * | 1/1998 | Coleman ..................... 715/523 |
| 6,259,977 B1 | 7/2001 | Mayer et al. | |
| 6,389,533 B1 * | 5/2002 | Davis et al. ................. 713/162 |
| 2004/0254893 A1* | 12/2004 | Tsuei et al. .................... 705/74 |
| 2004/0254894 A1* | 12/2004 | Tsuei et al. .................... 705/74 |
| 2004/0260653 A1* | 12/2004 | Tsuei et al. .................... 705/54 |

| 2007/0061393 A1* | 3/2007 | Moore ........................ 709/201 |

FOREIGN PATENT DOCUMENTS

| JP | 2006190244 A | * | 7/2006 |
| JP | 2006190244 A | * | 7/2006 |

OTHER PUBLICATIONS

Samarati et al., "Protecting Privacy when Disclosing Information: k-Anonymity and Its Enforcement through Generalization and Suppression," *SRI International, Technical Report* (1998).
Sweeney, "Datafly: a system for providing anonymity in medical data," *11th International Conference on Database Security* (1997).
Samarati et al., "Generalizing data to provide anonymity when disclosing information," *Proceedings of the Seventh ACM SIGACT-SIGMOD-SIGART Symposium on Principles of Data Systems* (1998).

(Continued)

*Primary Examiner*—Pierre Eddy Elisca
(74) *Attorney, Agent, or Firm*—Kirkpatrick & Lockhart Preston Gates Ellis LLP

(57) ABSTRACT

Systems and methods for deidentifying, or anonymizing, entries in an input data source are presented. According to one embodiment, the system includes a deidentification module for modifying entries in a version of the input data source to yield an output data source such that the entries of the output data source match a specified anonymity requirement. According to one embodiment, the resulting output data source may match the specified anonymity requirement with respect to a recipient profile that is input to the system. The deidentification module may further modify the entries in the version of the input data source such that the entries in the output data source are minimally distorted given the specified anonymity requirement.

30 Claims, 18 Drawing Sheets

OTHER PUBLICATIONS

Adam et al., "Security-control methods for statistical databases: a comparative study," *Computing Surveys* (1989).

Duncan et al., "Cell Suppression to limit content-based disclosure," *System Sciences* (1997).

Sweeney, L., "Guaranteeing anonymity when sharing medical data, the datafly system," *Massachusetts Institute of Technology Artificial Intelligence Laboratory, Working Paper No. AIWP-WP344*, May 1997.

Sweeney, L., "Guaranteeing anonymity when sharing medical data, the datafly system," *Proc. Journal of the American Medical Informatics Association*, 1997.

Sweeney, L., "Weaving technology and policy together to maintain confidentiality," *Journal of Law, Medicine and Ethics*. 1997, 25:98-110.

\* cited by examiner

| 970202 | 4973251 | n |
| 970202 | 7321785 | y |
| 970202 | 8324820 | n |
| 970203 | 2018492 | n |
| 970203 | 9353481 | y |
| 970203 | 3856592 | n |

| ZIP Code | Birthdate | Gender | Ethnicity |
|---|---|---|---|
| 33171 | 7/15/71 | m | Caucasian |
| 02657 | 2/18/73 | f | Black |
| 20612 | 3/12/75 | m | Asian |

| SSN | Ethnicity | Birth | Sex | ZIP |
|---|---|---|---|---|
| 819491049 | Caucasian | 10/23/64 | m | 02138 |
| 749201844 | Caucasian | 03/15/65 | m | 02139 |
| 819181496 | Black | 09/20/65 | m | 02141 |
| 859205893 | Asian | 10/23/65 | m | 02157 |
| 985820581 | Black | 08/24/64 | m | 02138 |

```
Core Algorithm
Input:      Private Table PT; quasi-identifier QI = (A_1, ..., A_n), k-anonymity constraint k; domain
            generalization hierarchies DGH_Ai, where i=1,...,n with accompanying functions f_Ai, and
            loss, which is a limit on the percentage of tuples that can be suppressed. PT[id] is the set
            of unique identifiers (key) for each tuple.
Output:     MGT a generalization of PT[QI] that enforces k-anonymity
Assumes:    |PT| ≥ k, and loss * |PT| = k
algorithm core:
// Construct a frequency list containing unique sequences of values across the quasi-identifier in PT,
// along with the number of occurrences of each sequence.
1. let freq be an expandable and collapsible Vector with no elements initially. Each element is of the
   form (QI, frequency, SID), where SID = {id_i : ∃t[id]∈PT[id]⇒t[id]=id_i}; and, frequency = |SID|.
   Therefore, freq is also accessible as a table over (QI, frequency, SID).
2. let pos ← 0, total ← 0
3. while total ≠ |PT| do
   3.1 freq[pos] ← (t[QI], occurs, SID)
         where t[QI]∈PT[QI], (t[QI],_,_)∉ freq; occurs = |PT| - |PT[QI] - {t[QI]}|;
         and, SID = {id_i : ∃t[id]∈PT[id]⇒t[id]=id_i}
   3.2 pos ← pos + 1, total ← total + occurs
// Make a solution by generalizing the attribute with the most number of distinct values
// and suppressing no more than the allowed number of tuples.
4. let belowk ← 0
5. for pos ← 1 to |freq| do
   5.1 (_, count) ← freq[pos]
   5.2 if count < k then do
       5.2.1 belowk ← belowk + count
6. if belowk > k then do:           // Note. loss * |PT| = k
   6.1 freq ← generalize(freq)
   6.2 go to step 4
7. else do
// assert: the number of tuples to suppress in freq is ≤ loss * |PT|
   7.1 freq ← suppress(freq, belowk)
   7.2 MGT ← reconstruct(freq)
8. return MGT.
```

Fig. 7

```
algorithm reconstruct(freq):
// This algorithm produces a table based on the tuples within freq and their reported frequencies.
1. let T ← ∅     // T is a table and so it is a multiset, which maintains duplicates
3. for pos ← 1 to |freq| do:
       4.1 (t, count, sid) ← freq[pos]
       4.2 for each id ∈ sid do:
           4.2.1  T ← T ∪ {t[QI, id]}
5  return T
```

Fig. 10

```
           generalize Algorithm
// This algorithm identifies the attribute within the quasi-identifier having the most number of distinct
// values in the tuples stored in freq and then generalizes those values in freq. Generalization is
// enforced at the attribute level, so all the values associated with an attribute are in the same domain.
1. let max ← 0
2. for each a ∈ QI do:
       2.1 let values ← ∅
       2.2 for pos ← 1 to |freq| do:
              2.2.1  (t, __, __) ← freq[pos]
              2.2.2  values ← values ∪ { t[a] }
       // assert: values contains set of values assigned to attribute a in the tuples of freq
       2.3 if max < |values| then do:
              2.3.1    max ← |values|
              2.3.2    attr ← a
// assert: attr is the attribute of QI having the most number of distinct values (max) in the tuples of freq
3. let V be a frequency list of the same type as freq. V initially has no elements.
4. if max = 1 then do:
       4.1 halt on error    // |PT| < k
// generalize values assigned to attr
5. for pos ← 1 to |freq| do:
       5.1 ([$v_{a1}$, ..., $v_{an}$], count, sid) ← freq[pos]
       5.2 if attr = $a_1$ then do
              5.2.1   V ← VectorAdd(V, [$f_{attr}(v_{a1})$,...,$v_{an}$], count, sid)
       5.3 else if attr = $a_n$ then do:
              5.3.1   V ← VectorAdd(V, [$v_{a1}$,...,$f_{attr}(v_{an})$], count, sid)
       5.4 else V ← VectorAdd(V, [$v_{a1}$,...,$f_{attr}(v_{attr})$,...,$v_{an}$], count, sid)
6. freq ← V
7. return freq
```

Figure 8

```
        VectorAdd Algorithm
Input:      V, t, occurs, sid
Output:     Updates and returns V, a frequency list
// This method adds the tuples associated with (t,occurs,sid) to V avoiding duplication
algorithm VectorAdd:
1. for pos ← 1 to |V| do:
       1.1. let ($t_l$, $occurs_l$, $sid_l$) ← V[pos]
       1.2. if $t_l$ = t then do:
              1.2.1.  V[pos] ← (t, occurs + $occurs_l$, $sid_l$ ∪ sid)
              1.2.2.  return V
2. V[pos+1] ← (t, occurs, sid)  // add to end
3. return V
```

Figure 11

```
algorithm suppress(freq, belowk):
// This algorithm suppresses the tuples within freq that do not satisfy the k requirement; these
// should total belowk number of tuples.
// Assume freq has no more than loss * |PT| tuples to suppress, and loss * |PT| = k.
1. let smallest ← |PT|
2. for pos ← 1 to |freq| do:
        2.1  (t, count,__) ← freq[pos]
        2.2  if count < k then do:
               2.2.1   freq[pos] ← (null, count,__)
                        where null is the suppressed values for the tuple
               2.2.2.  belowk ← belowk – count
        2.3  else do:
               2.3.1   if count < smallest then do:
                         2.3.1.1  smallest ← count
3  if (belowk > 0) and (belowk < k) then do:    // Note. loss * |PT| = k, belowk ≤ k
        3.1  (t, count,__) ← freq[smallest]
        3.2  if (count – belowk) ≥ k then do:
               3.2.1   freq[pos+1] ← (t, count-belowk,__)
               3.2.2   freq[smallest] ← (null, belowk,__)
        3.3  else do:
               3.3.1   freq[smallest] ← (null, count,__)
4   return freq
```

Figure 9

|    | Race  | Birthdate | Gender | ZIP   | Problem        |
|----|-------|-----------|--------|-------|----------------|
| t1 | black | 9/1965    | male   | 02141 | short of breath |
| t2 | black | 2/1965    | male   | 02141 | chest pain     |
| t3 | black | 10/1965   | female | 02138 | painful eye    |
| t4 | black | 8/1965    | female | 02138 | wheezing       |
| t5 | black | 11/1964   | female | 02138 | obesity        |
| t6 | black | 12/1964   | female | 02138 | chest pain     |
| t7 | white | 10/1964   | male   | 02138 | short of breath |
| t8 | white | 3/1965    | female | 02139 | hypertension   |
| t9 | white | 8/1964    | male   | 02139 | obesity        |
| t10| white | 5/1964    | male   | 02139 | fever          |
| t11| white | 2/1967    | male   | 02138 | vomiting       |
| t12| white | 3/1967    | male   | 02138 | back pain      |

Figure 12

| Race  | Birthdate | Gender | ZIP   | Problem         |
|-------|-----------|--------|-------|-----------------|
| black | 1965      | male   | 02141 | short of breath |
| black | 1965      | male   | 02141 | chest pain      |
| black | 1965      | female | 02138 | painful eye     |
| black | 1965      | female | 02138 | wheezing        |
| black | 1964      | female | 02138 | obesity         |
| black | 1964      | female | 02138 | chest pain      |
| white | 1964      | male   | 02139 | obesity         |
| white | 1964      | male   | 02139 | fever           |
| white | 1967      | male   | 02138 | vomiting        |
| white | 1967      | male   | 02138 | back pain       |

Figure 14

ZIP code

Gender

Race

Birth Date

|    | Race  | Birthdate | Gender | ZIP   | # occurs |
|----|-------|-----------|--------|-------|----------|
| t1 | black | 9/20/65   | male   | 02141 | 1        |
| t2 | black | 2/14/65   | male   | 02141 | 1        |
| t3 | black | 10//23/65 | female | 02138 | 1        |
| t4 | black | 8/24/65   | female | 02138 | 1        |
| t5 | black | 11/7/64   | female | 02138 | 1        |
| t6 | black | 12/1/64   | female | 02138 | 1        |
| t7 | white | 10/23/64  | male   | 02138 | 1        |
| t8 | white | 3/15/65   | female | 02139 | 1        |
| t9 | white | 8/13/64   | male   | 02139 | 1        |
| t10 | white | 5//5/64  | male   | 02139 | 1        |
| t11 | white | 2/13/67  | male   | 02138 | 1        |
| t12 | white | 3/21/67  | male   | 02138 | 1        |
|    | 2     | 12        | 2      | 3     |          |

Figure 15

|         | Race  | Birthdate | Gender | ZIP   | # occurs |
|---------|-------|-----------|--------|-------|----------|
| t1, t2  | black | 1965      | male   | 02141 | 2        |
| t3, t4  | black | 1965      | female | 02138 | 2        |
| t5, t6  | black | 1964      | female | 02138 | 2        |
| t7, t8  | white | 1964      | male   | 02138 | 2        |
| t9, t10 | white | 1964      | male   | 02139 | 2        |
| t11,t12 | white | 1967      | male   | 02138 | 2        |
|         | 2     | 3         | 2      | 3     |          |

Figure 16

```
k-Similar Algorithm
Input:      Table T; quasi-identifier QI = (A_1, ..., A_n), k-anonymity constraint k; and domain and
            value generalization hierarchies DGH_Ai and VGH_Ai, where i=1,...,n with accompanying
            functions f_Ai.
Output:     A k-minimal distortion of T[QI]
Assume:     |T| ≥ k
algorithm k-Similar:
1.  Append an attribute ID to T. The associated values of ID in T are key identifiers that are unique for
    each tuple of T; these values are numbered from 1 to |T|.
2.  clique = CliqueConstruct( T[QI,ID] )
3.  clusts ← kSimilarRun(T, k, clique)
4.  return TableConstruct(clusts)
```

Figure 18

```
CliqueConstruct
Input:      Table T[QI,ID]; where quasi-identifier QI = (A_1, ..., A_n), ID associates unique values
            numbered from 1 to |T| to the tuples of T, and value generalization hierarchies VGH_Ai
            and VGH_Ai, where i=1,...,n with accompanying functions f_Ai.
Output:     clique, which is a clique of the tuples of T stored in a 2-dimensional array. Each node in
            the clique is a tuple. Each edge records the distance vector that corresponds to the
            distance between the tuples whose nodes are incident.
algorithm CliqueConstruct:
1.  let clique be an initially empty 2-dimensional square array of size |T| by |T|.
    2.1  for tuplefrom ← 1 to |T| do:
        2.1.1  for tupleto ← 1 to |T| do:
            2.1.1.1  if (tuplefrom ≠ tupleto) then:
                2.1.1.1.1  clique[tuplefrom, tupleto]
                            ← Distance(T[QI,ID=tuplefrom], T[QI,ID=tupleto])
2.  return clique
```

Figure 19

```
Distance
Input:      t_1,t_2 ∈ T[QI]; where quasi-identifier QI = (A_1, ..., A_n), and value generalization hierarchies
            VGH_Ai, where i=1,...,n with accompanying functions f_Ai.
Output:     [d_1, ..., d_n], which is a distance vector that corresponds to the distance between the tuples
            t_1 and t_2.
algorithm Distance:
1.  DV ← [d_1,...,d_n] where each d_i is the length of the unique path between t_1[A_i] and t_2[A_i] in VGH_Ai for i=1...n
2.  return DV
```

Figure 20

```
kSimilarRun Algorithm
Input:       Table T[QI,ID], where quasi-identifier QI = ($A_1, ..., A_n$), ID associates unique values
             numbered from 1 to |T| to the tuples of T; k-anonymity constraint k; value generalization
             hierarchies $VGH_{Ai}$, where $i=1,...,n$ with accompanying functions $f_{Ai}$; and, clique, which
             is a clique of the tuples of T where each node in the clique is a tuple and each edge
             records the distance vector that corresponds to the distance between the tuples whose
             nodes are incident.
Output:      clusts, which is a vector of sets of ID values of tuples. Each member set identifies a
             cluster of tuples that when generalized to respect to the distance vectors incident to the
             tuples provide a set of "closest" tuples in a k-minimal distortion of T[QI]
algorithm kSimilarRun:
1.  if |T| = 0 then return ∅
2.  if |T| < k then error "Table must have at least k elements"
3.  if |T| < 2*k then return { T[ID] }            // make a cluster containing all tuples in T
4.  mins ← GenerateMinimums(T[QI,ID], clique, k)
5.  complements ← FindComplements(mins)
6.  if |complements| > 0 then do:
    6.1  let $T_2$ be a table with no elements initially
    6.2  for pos ← 1 to |complements| do:
         6.2.1  $T_2$ ← { t[QI,ID] | t[QI,ID]∈T[QI,ID∈ complements[pos]] }
         6.2.2  T ← T – $T_2$
         6.2.3  if ( |T| > 0 ) then do: mins ← GenerateMinimums(T[QI,ID], clique, k)
7.  return complements ∪ kSimilarRunParts( T, mins )
```

Figure 21

```
TableConstruct
Input:       clusts, which is a vector of sets of ID values of tuples. Each member set identifies a
             cluster of tuples that when generalized to respect to the distance vectors incident to the
             tuples provide a set of "closest" tuples in a k-minimal distortion of T[QI], where quasi-
             identifier QI = ($A_1, ..., A_n$), ID associates unique values numbered from 1 to |T| to the
             tuples of T, and clique, which is a clique of the tuples of T where each node in the clique
             is a tuple and each edge records the distance vector that corresponds to the distance
             between the tuples whose nodes are incident.
Output:      GT, which is a minimal generalization of T[QI]. Tuples identified within an element of
             clusts are generalized to have the same values.
algorithm TableConstruct:
1.  let GT ← ∅
2.  for clustnum ← 1 to |clusts| do:
    2.1  let V         be a distance vector of the form [$d_1, ..., d_n$] where each $d_i$=0
                       and n is the number of attributes in the quasi-identifier QI = ($A_1, ..., A_n$)
    2.2  let aclust    be an expandable and collapsible Vector whose elements
                       are initialized to clusts[clustnum]
    2.3  for tupleto ← 2 to |aclust| do:
         2.4.1  V ← V ⊕ clique[ aclust[1], aclust[tupleto] ]      // compute maximal distance vector
    2.4  for t ← 1 to |aclust| do:
         2.5.1  GT ← GT ∪ GeneralizeTuple(T[QI,ID=t], V)          // generalize each tuple in cluster
3.  return GT
```

Figure 22

GenerateMinimums Algorithm

Input: Table T[QI,ID]; where quasi-identifier QI = $(A_1, ..., A_n)$, ID associates unique values numbered from 1 to |T| to the tuples of T, $k$-anonymity constraint $k$, and clique, which is a clique of the tuples of T where each node in the clique is a tuple and each edge records the distance vector that corresponds to the distance between the tuples whose nodes are incident.

Output: *mins*, which is a Vector of sets of ID values of tuples. Each member set identifies a cluster of $k-1$ of $t$'s closest tuples. Each member set includes $t$ so the total cluster size is $k$.

algorithm GenerateMinimums:
1. let *mins* be an expandable and collapsible Vector with no elements initially.
2. let *stack* be an empty Stack.
3. let *zero* be a distance vector $[d_1, ..., d_n]$ where each $d_i=0$ and $n$ is the number of attributes in the quasi-identifier QI = $(A_1, ..., A_n)$
4. for *tupleto* ← 1 to |clique| do:
   4.1 mins = traverse(*tupleto*, *tupleto*+1, k, {*tupleto*}, zero, ∞, mins)
           // stack *and* clique *are globally available across iterations of* traverse()
5. return *mins*

Figure 23

Traverse Algorithm
Input: (*node, next, k, path, mV, mdist, mins*)

*node*    which is the unique value associated with a tuple in clique that represents the tuple "from" which distance will be measured to *next* on this iteration.

*next*    which is the unique value associated with a tuple in clique that represent the tuple "to" which distance will be measured from *node* on this iteration.

*k*    which is the *k*-anonymity constraint

*path*    which is the set of tuples comprising the shortest path from *node* to the tuple that serves as the root of the traversal $mV_t$    which is a maximal distance vector from the tuple that serves as the root of the traversal to *node*.

*mdist*    which is the measure of distortion from the root of the traversal to *node*. It does not include the distance from *node* to *next*.

*mins*    which is a Vector of sets of ID values of tuples computed so far. Each member set identifies a cluster of $k-1$ of *t*'s closest tuples. Each member set includes *t* so the total cluster size is *k*. At the end of the traversal this value provides the answer. It is shared across iterations to track global information.

Output:    *mins*, which is a Vector of sets of ID values of tuples. Each member set identifies a cluster of $k-1$ of *t*'s closest tuples. Each member set includes *t* so the total cluster size is *k*.

Assumes    dist() function exists and computes non-negative distance from a distance vector based on *Prec*(), can be weighted or not.
Assumes following exist and are globally available:

*stack*    which is a Stack that contains information on each node from the root of the traversal up to, but not including *node*. Each element of the stack contains values of the form: (*node, path, mV, mdist*). It is shared across iterations to track global information.

*clique*    which is a clique of the tuples of T where each node in the clique is a tuple and each edge records the distance vector that corresponds to the distance between the tuples whose nodes are incident, *t*, which is an ID value unique to a tuple in T.

algorithm Traverse:
1. if (*next* > |clique|) and stackEmpty() then do:
    1.1. return *mins*
2. else if (*next* > |clique|) then do:
    2.1. ($root_0, path_0, mV_0, mdist_0$) ← stackPop()
    2.2. return traverse($root_0$, *node*+1, *k*+1, $path_0$, *mins*)
3. else if (*next* ∈ T[ID]) then do:
    3.1. return traverse(*node, next*+1, 1, *path, mV, mdist, mins*)
4. $V_I$ ← $mV$ ⊕ clique[*node, next*]
5. $d_I$ ← dist($V_I$) * (|*path*| + 1)
6. $p_I$ ← *path* ∪ {*next*}
7. if ($d_I$ > *mdist*) then do:
    7.1. return traverse(*node, next*+1, *k, path, mV, mdist, mins*)
8. else if (*k* ≡ 1) and ($d_I$ ≡ *mdist*) then do:
    8.1. *mins*[ |*mins*| + 1] ← $p_I$
    8.2. return traverse(*node, next*+1, 1, *path, mV, mdist, mins*)
9. else if (*k* ≡ 1) then do:    // and ($d_I$ < mdist) *is implied*
    9.1. purge all elements from *mins*
    9.2. *mins*[1] ← $p_I$
    9.3. *mdist* ← $d_I$
    9.4. *mV* ← $V_I$
    9.5. return traverse(*node, next*+1, 1, *path, mV, mdist, mins*)
10. else do:    // *k* ≠ 1 *is implied*
    10.1. stackPush(*next*, $p_I$, $V_I$, $d_I$)
    10.2. return traverse(*next, next*+1, *k*-1, $p_I$, $V_I$, $d_I$, *mins*)

Figure 24

```
FindComplements Algorithm
Input:      mins, which is a set of sets of ID values of tuples. Each member set identifies a cluster of
            k-1 of t's closest tuples. Each member set includes t so the total cluster size is k.
Output:     distincts, which is a vector of sets of ID values of tuples. Each member set identifies a
            cluster that can be partitioned as an independent sub-solution.
algorithm FindComplements:
1. let distincts be an expandable and collapsible Vector with no elements initially.
2. let allnodes ← ∅
3. for pos ← 1 to |mins| do:
     3.1   allnodes ← allnodes ∪ mins[pos]
4. for candidate ← 1 to |mins| do:
     4.1   let s ← allnodes - mins[candidate]
     4.2   for pos ← 1 to |mins| do:
             4.1.1  temp ← mins[pos] ∩ mins[candidate]
             4.1.2  if ( temp ≠ ∅) then do:
                      4.2.1.1. s ← s - temp
     4.3.  if (s ≡ allnodes - mins[candidate] ) then do:
             4.3.1  distincts[ |distincts| + 1] ← mins[candidate]
5. return distincts
```

Figure 25

```
kSimilarRunParts Algorithm
Input:      Table T[QI,ID]; where quasi-identifier QI = (A_1, ..., A_d), ID associates unique values
            numbered from 1 to |T| to the tuples of T, and mins, which is a vector of sets of ID values
            of tuples. Each member set identifies a cluster of k closest tuples.
Output:     clusts, which is a vector of sets of ID values of tuples. Each member set identifies a
            cluster of tuples that when generalized to respect to the distance vectors incident to the
            tuples provide a set of "closest" tuples in a k-minimal distortion of T[QI]. Executes
            kSimilarRun() mutually recursively, on connected groups within mins.
algorithm kSimilarRunParts:
1. if (T ≡ ∅) then return ∅
2. (T_1, mins1, T_2, mins2) ← Partition(T, mins)
3. if (|T_1| < 2*k) then do:
     3.1   return kSimilarRun(T_1) ∪ kSimilarRunParts(T_2, mins2)
4. else do:
     // assert: there exist tuple(s) common to all elements within partition T_1, based on mins1
     4.1   withheld ← CommonTuples(mins1, clique)
     4.2   if ( (|T_1| - |withheld|) < 2*k) then do:
             4.2.1  return addTuple(withheld, k,(mins1-withheld), clique)
                          ∪ kSimilarRunParts(T_2, mins2)
     4.3   mins3 ← kSimilarRun(T_1[QI,ID∉ withheld], k, clique)
     4.4   return addTuple(withheld, k, mins3, clique) ∪ kSimilarRunParts(T_2, mins2)
```

Figure 26

```
Partition Algorithm
Input:      Table T[QI,ID]; where quasi-identifier QI = (A₁, ..., Aₙ), ID associates unique values
            numbered from 1 to |T| to the tuples of T; and, mins, which is a set of sets of ID values of
            tuples. Each member set identifies a cluster of k-1 of t's closest tuples. Each member set
            includes t so the total cluster size is k.
Output:     (T₁, T₂, ms), where T₁ ∪ T₂ = T and T₁ ∩ T₂ = ∅. The tuples of T₁ identifies a
            connected group of tuples that can be partitioned as an independent sub-solution. This
            decision is based on the connectedness of elements within mins. The identifier ms
            contains the subset of mins not accounted for by the tuples of T₁.
algorithm Partition:
1.  let allnodes ← ∅, ms ← ∅
2.  for pos ← 1 to |mins| do:
    2.1  allnodes ← allnodes ∪ mins[pos]
3.  let r ← mins[1]              // test connectedness of mins[1]
4.  for pos ← 2 to |mins| do:
    4.1  if ( mins[pos] ∩ r ≠ ∅) then do:
        4.1.1  r ← r ∪ mins[pos]
    4.2  else do:
        4.2.1  ms ← ms ∪ mins[pos]
5.  if ( mins ≠ r ) then do:
    5.1  return (T₁, r, T₂, ms) where T₁ = {tᵢ | tᵢ ∈ T[QI,ID=tⱼ] and tⱼ∈ r} and T₂ = T-T₁
6   else do:
    6.1  return (T, r, ∅, ∅)
```

Figure 27

```
CommonTuples Algorithm
Input:      mins, which is a set of sets of ID values of tuples. Each member set identifies a cluster of
            k-1 of t's closest tuples. Each member set includes t so the total cluster size is k; and,
            clique, which is a clique of the tuples of T where each node in the clique is a tuple and
            each edge records the distance vector that corresponds to the distance between the tuples
            whose nodes are incident, t, which is an ID value unique to a tuple in T
Output:     withheld, which is a set of unique value associated with a tuple in T and that occurs in
            each element of mins thereby making them "the" closest tuple to all tuples.
algorithm CommonTuples:
1.  let withheld ← ∅
2.  for tnum ← 1 to |clique| do:
    2.1  let inall ← true
    2.2  for pos ← 1 to |mins| do:
        2.2.1  if (tnum ∉ mins[pos])
            2.2.1.1  inall ← false
    2.3  if ( inall = true ) then do:
        2.3.1  withheld ← withheld ∪ {tnum}
3.  return withheld
```

Figure 28

| AddTuple | |
|---|---|
| Input: | *withheld*, which is a set of unique values associated with tuples in T; *k*-anonymity constraint *k*; *clusts*, also known as *mins*, is a vector of sets of ID values of tuples. Each member set identifies a cluster of tuples that when generalized to respect to the distance vectors incident to the tuples provide a set of "closest" tuples in a *k*-minimal distortion of T[QI], where quasi-identifier QI = $(A_1, ..., A_n)$. ID associates unique values numbered from 1 to m to the tuples of T; and, *clique*, which is a clique of the tuples of T where each node in the clique is a tuple and each edge records the distance vector that corresponds to the distance between the tuples whose nodes are incident. |
| Output: | *clusts*, which is a vector of sets of ID values of tuples that is the same as the original value of *clusts* (also known as *mins*) provided to the algorithm except the returned value has an element that includes the elements of *withheld*. The tuple(s) identified in *withheld* replace tuple(s) in an original element of *clusts* such the overall loss of precision due to generalization is minimized and all tuples remain included. | algorithm AddTuple:
1. let $d \leftarrow \infty, n \leftarrow 0, c \leftarrow \emptyset$
2. for *clustnum* $\leftarrow$ 1 to |*clusts*| do:
   1.1 if *clusts*[*clustnum*] $\equiv 2 * k$ - |*withheld*| then do:
      1.1.1 *testclust* $\leftarrow$      be an expandable and collapsible Vector whose elements are initialized to *clusts*[*clustnum*]
      1.1.2 $(d_1, c_1) \leftarrow$ addTupleMin(*withheld*, *testclust*, k, d, c, clique)
      1.1.3 if $(d_1 < d)$ then do:
         1.1.1.1. $d \leftarrow d_1$
         1.1.1.2. $n \leftarrow$ *clustnum*
         1.1.1.3. $c \leftarrow c_1$
3. *temp* $\leftarrow$ *clusts*[*n*] $\cup$ *withheld*
4. *clusts*[*n*] $\leftarrow$ *temp* $- c$
5. *clusts*[ |*clusts*|+1 ] $\leftarrow c$
6. return *clusts*

Figure 29

|    | A1       | A2        | A3       |
|----|----------|-----------|----------|
|    | Home Zip | Hosp. ZIP | Work Zip |
| t1 | 02138    | 02138     | 02138    |
| t2 | 02138    | 02139     | 02138    |
| t3 | 02138    | 02138     | 02141    |
| t4 | 02138    | 02139     | 02139    |

|    | A1       | A2        | A3       |
|----|----------|-----------|----------|
|    | Home Zip | Hosp. ZIP | Work Zip |
| t1 | 02138    | 02138     | 021**    |
| t2 | 02138    | 02139     | 0213**   |
| t3 | 02138    | 02138     | 021**    |
| t4 | 02138    | 02139     | 0213**   |

| {t1, t2} |
| {t2, t4} |
| {t1, t3} |

SYSTEMS AND METHODS FOR DEIDENTIFYING ENTRIES IN A DATA SOURCE

CROSS-REFERENCE TO RELATED APPLICATIONS

This application claims priority under 35 U.S.C. § 119 to U.S. provisional patent application Ser. No. 60/282,708, filed Apr. 10, 2001, which is incorporated herein by reference.

BACKGROUND OF THE INVENTION

Today's globally networked society places great demand on the dissemination and sharing of person-specific data for many new and exciting uses. Even situations where aggregate statistical information was once the reporting norm now rely heavily on the transfer of microscopically detailed transaction and encounter information. This happens at a time when more and more historically public information is also electronically available. When these data are linked together, they provide an electronic shadow of a person or organization that is as identifying and personal as a fingerprint—even when the information contains no explicit identifiers such as name or phone number. Other distinctive data, such as birth date or zip code often combine uniquely and can be linked to publicly available information to reidentify individuals. Producing anonymous data that remains specific enough to be useful is often a very difficult task, and practice today tends to either incorrectly believe confidentiality is maintained when it is not or produces data that are practically useless.

One type of commonly shared data is electronic medical records. Analysis of the detailed information contained within electronic medical reports promises advantages to society, including improvements in medical care, reduced institution cost, the development of predictive and diagnosis support systems and the integration of applicable data from multiple sources into a unified display for clinicians. These benefits, however, require sharing the contents of medical records with secondary viewers, such as researchers, economists, statisticians, administrators, consultants, and computer scientists, to name a few. The public would probably agree that these secondary parties should know some of the information buried in the records, but that such disclosures should not risk identifying patients.

There are three major difficulties in providing anonymous data. One of the problems is that anonymity is in the eye of the beholder. Consider an HIV testing center located in a heavily populated community within a large metropolitan area. If the table shown in FIG. 1 shows the results for two days of testing, then it may not appear very anonymous if the left-most column is the date, the middle column is the patient's phone number and the right-most column holds the results. An electronic phone directory can match each phone number to a name and address. Although this does not identify the specific member of the household tested, the possible choices have narrowed to a particular address.

Alternatively, if the middle column in the table of FIG. 1 holds random numbers assigned to samples, then identifying individuals becomes more difficult, but still cannot guarantee the data are anonymous. If a person with inside knowledge (e.g., a doctor, a patient, a nurse, an attendant, or even a friend of the patient) recognizes a patient and recalls the patient was the second person tested that day, then the results are not anonymous to the insider. In a similar vein, medical records distributed with a provider code assigned by an insurance company are often not anonymous because thousands of administrators often have directories that link the provider's name, address and phone number to the assigned code.

As another example, consider the table of FIG. 2. If the contents of this table are a subset of an extremely large and diverse data source, then the three records listed in the table at FIG. 2 may appear anonymous. Suppose the zip code 33171 primarily consists of a retirement community; then there are very few people of such a young age living there. Likewise, 02657 is the zip code for Provincetown, Mass., in which there may be only about five black women living there year-round. The zip code 20612 may have only one Asian family. In these cases, information outside the data identifies the individuals.

Most towns and cities sell locally-collected census data or voter registration lists that include the date of birth, name and address of each resident. This information can be linked to medical data that include a date of birth and zip code, even if the names, social security numbers and addresses of the patients are not present. Of course, census data are usually not very accurate in college towns and in areas that have a large transient community, but for much of the adult population in the United States, local census information can be used to reidentify deidentified data since other personal characteristics, such as gender, data of birth and zip code, often combine uniquely to identify individuals.

A second problem with producing anonymous data concerns unique and unusual information appearing within the data themselves. Consider the data source shown in the table of FIG. 3. It is not surprising that the social security number is uniquely identifying, or given the size of the illustrated data source, that the birth date is also unique. To a lesser degree, the zip code identifies individuals since it is almost unique for each record. Importantly, what may not have been known without close examination of the particulars of this data source is that the designation of Asian ethnicity is uniquely identifying. Any single uniquely occurring value can be used to identify an individual. Remember that the unique characteristic may not be known beforehand. It could be based on diagnosis, achievement, birth year, visit date, or some other detail or combination of details available to the memory of a patient or a doctor, or knowledge about the data source from some other source.

Measuring the degree of anonymity in released data poses a third problem when producing anonymous data for practical use. The Social Security Administration (SSA) releases public-use files based on national samples with small sampling fractions (usually less than 1 in 1,000). The files contain no geographic codes, or at most regional or size of place designators. The SSA recognizes that data containing individuals with unique combinations of characteristics can be linked or matched with other data sources. Thus, the SSA's general rule is that any subset of the data that can be defined in terms of combinations of characteristics must contain at least five individuals. This notion of a minimal bin size, which reflects the smallest number of individuals matching the characteristics, is useful in providing a degree of anonymity within data: the larger the bin size, the more anonymous the data. As the bin size increases, the number of people to whom a record may refer also increases, thereby masking the identity of the actual person.

In medical data sources, the minimum bin size should be much larger than the SSA guidelines suggest for three reasons: (1) most medical data sources are geographically located and so one can presume, for example, the zip codes of a hospital's patients; (2) the fields in a medical data source provide a tremendous amount of detail and any field can be a candidate for linking to other data sources in an attempt to reidentify patients; and (3) most releases of medical data are not randomly sampled with small sampling fractions, but instead include most, if not all of the data source.

Determining the optimal bin size to ensure anonymity is not a simple task. It depends on the frequencies of characteristics found within the data as well as within other sources for reidentification. In addition, the motivation and effort required to reidentify release of data in cases where virtually all-possible candidates can be identified must be considered. For example, if data are released that map each record to ten possible people, and the ten people can be identified, then all ten candidates may be contacted or visited in an effort to locate the actual person. Likewise, if the mapping is 1 in 100, all 100 could be phoned because visits may be impractical, and in the mapping of 1 in 1,000, a direct mail campaign could be employed. The amount of effort the recipient is willing to spend depends on their motivation. Some medical files are quite valuable, and valuable data will merit more effort. In these cases, the minimum bin size must be further increased or the sampling fraction reduced to render those efforts useless.

The above-described anonymity concerns implicated upon the dissemination and sharing of person-specific data must be countenanced with the fact that there is presently unprecedented growth in the number and variety of person-specific data collections and in the sharing of this information. The impetus for this explosion has been the proliferation of inexpensive, fast computers with large storage capacities operating in ubiquitous network environments.

There is no doubt that society is moving toward an environment in which society could have almost all the data on all the people. As a result, data holders are increasingly finding it difficult to produce anonymous and declassified information in today's globally networked society. Most data holders do not even realize the jeopardy at which they place financial, medical, or national security information when they erroneously rely on security practices of the past. Technology has eroded previous protections leaving the information vulnerable. In the past, a person seeking to reconstruct private information was limited to visiting disparate file rooms and engaging in labor-intensive review of printed material in geographically distributed locations. Today, one can access voluminous worldwide public information using a standard hand-held computer and ubiquitous network resources. Thus, from seemingly anonymous data and available public and semi-pubic information, one can often draw damaging inferences about sensitive information. However, one cannot seriously propose that all information with any links to sensitive information be suppressed. Society has developed an insatiable appetite for all kinds of detailed information for many worthy purposes, and modern systems tend to distribute information widely.

BRIEF SUMMARY OF THE INVENTION

In one general respect, the present invention is directed to a system for deidentifying entries in a data source. Deidentifying is sometimes also referred to as anonymizing. According to one embodiment, the system comprises a deidentification module. The deidentification module is for copying and then modifying entries in the copied version of the data source (an input data source) to yield an output data source such that the entries of the output data source match a specified anonymity requirement. According to one embodiment, the resulting output data source may match the specified anonymity requirement with respect to a recipient profile that the system may receive as an input. The deidentification module may modify the entries by, for example, generalizing, suppressing or replacing the entries in the copy of the input data source as appropriate to satisfy the specified anonymity requirement. According to another embodiment, the deidentification module may modify entries in the copy of the input data source such that the entries in the resulting output data source are minimally distorted given the specified anonymity requirement.

In another general respect, the present invention is directed to a method for deidentifying (or anonymizing) entries in the input data source. According to one embodiment, the method includes receiving a specified anonymity requirement. The method further includes copying and then modifying entries in the copy of the input data source such that the entries in the resulting output data source match the specified anonymity requirement. According to one embodiment, the resulting output data source may match the specified anonymity requirement with respect to a recipient profile that may be received as an input. Modifying the entries in the copy of the input data source may include, for example, generalizing, suppressing or replacing entries where appropriate to satisfy the specified anonymity requirement. According to another embodiment, the method may include modifying the entries in the input data source such that entries in the resulting output data source are additionally minimally distorted given the specified anonymity requirement.

In another general respect, the present invention is directed to a computer readable medium. The computer readable medium may have stored thereon instructions, which when executed by a processor, cause the processor to read a specified anonymity requirement. The computer readable medium may also cause the processor to copy and then modify entries in the copy of the input data source to yield an output data source having entries that match the specified anonymity requirement. According to another embodiment, the computer readable medium may cause the processor to also read a specified recipient profile, and then modify the entries in the copy of the input data source to match the specified anonymity requirement with respect to the received recipient profile. The computer readable medium may cause the processor to modify the entries in the copy of the data source by, for example, generalizing, suppressing or replacing entries where appropriate to satisfy the anonymity requirement. According to one embodiment, the computer readable medium may cause the processor to modify the entries in the copy of the input data source such that the entries in the resulting output data source are minimally distorted given the specified anonymity requirement.

BRIEF DESCRIPTION OF THE FIGURES

Embodiments of the present invention are described in conjunction with the following figures, wherein:

FIGS. 7-11 are charts listing algorithms of the deidentification module according to embodiments of the present invention;

FIGS. 12 and 14-16 illustrate an example of how the deidentification module operates according to one embodiment of the present invention;

FIGS. 18-29 are charts listing algorithms for the deidentification module according to another embodiment of the present invention.

DETAILED DESCRIPTION OF THE INVENTION

It is to be understood that the figures and descriptions of the following embodiments have been simplified to illustrate elements that are relevant for a clear understanding of the present invention, while eliminating, for purposes of clarity, other elements. For example, certain operating system details and modules of computer processing devices are not described herein. Those of ordinary skill in the art will recognize, however, that these and other elements may be desirable. However, because such elements are well known in the art, and because they do not facilitate a better understanding of the present invention, a discussion of such elements is not provided herein.

Figure 4:
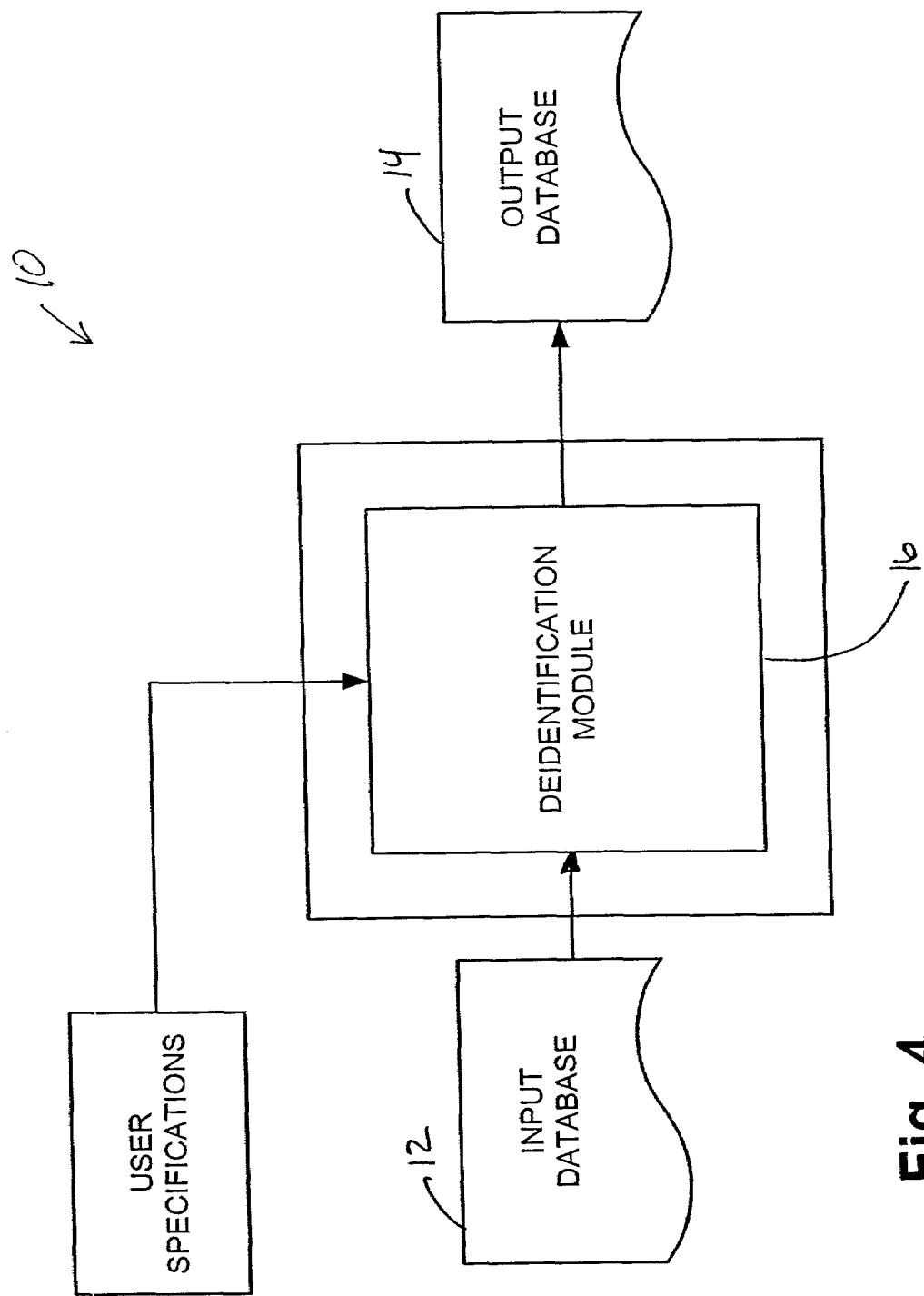

FIG. 4 is a block diagram of a system 10 for deidentifying (or anonymizing) entries in a data source according to one embodiment of the present invention. The system 10 maintains anonymity in entity-specific data by automatically generalizing, substituting and removing information as appropriate without losing many of the details found, for example, within the data. As used herein, the term "data source" refers to a database or to any field-structured data, such as a table, a spreadsheet, a text file organized as a table, or a data stream where the data is organizable as a table. A table may have rows ("tuples" or "records") and columns ("attributes" of "fields"). The system 10, according to one embodiment, may receive certain user specifications including, for example, specific fields and records, a profile of the recipient of the data, and a minimum anonymity level. Based on the user specifications, the system 10 may alter entries in a version (such as a copy that is read as an input) of the input electronic data source 12, which may contain privately held data, to produce the resulting output electronic data source 14, whose information matches the specified anonymity level with respect to the recipient profile, according to such an embodiment. The output 14 could be a modification of the input 12. The input data source 12 may be stored, for example, in a data source server (not shown) and the output data source 14 may be displayed for the recipient by a display device (not shown), stored in the same or another data source server, or a hard-copy version of the output data source 14 may be created for use by the recipient. The input data source 12 may contain, for example, any type of field-structured data including, but not limited to, medical records and related medical information.

The system 10 may be implemented as a computing device such as, for example, a personal computer, a laptop computer, a workstation, a minicomputer, a mainframe, a handheld computer, a small computer device, or a supercomputer, depending upon the application requirements. As illustrated in FIG. 4, the system 10 may include a deidentification module 16. As described in more detail, the deidentification module 16 may produce the output data source 14 from the input data source 12 based on the user specifications. The module 16 maybe implemented as software code to be executed by a processor (not shown) of the system 10 using any suitable computer language such as, for example, Java, C or C++ using, for example, conventional or object-oriented techniques. The software code may be stored as a series of instructions or commands on a computer readable medium, such as a random access memory (RAM), a read only memory (ROM), a magnetic medium such as a hard-drive or a floppy disk, or an optical medium such as a CD-ROM.

Figures 1, 2, 3, 5:
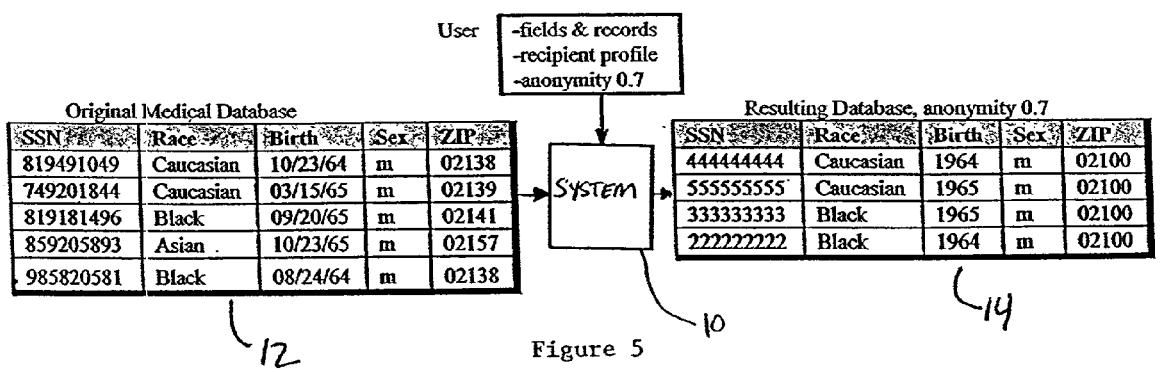
FIGS. 1-3 are sample data tables.
FIGS. 4 and 5 are diagrams illustrating a system for deidentifying entries in a data source according to one embodiment of the present invention.

FIG. 5 provides an example of how the system 10 works according to one embodiment. The input data source 12 is shown on the left. In the illustrated embodiment, the user (e.g., data holder) specifies, for example, the attributes and tuples for release, the recipient profile, and the anonymity level (in this example 0.7). These user specifications may be input to the deidentification module 16 via, for example, a user interface (not shown) of the system 10. The deidentification module 16 may make a copy of the input data source 12, and then generate the output data source 14 according to, for example, the methods described herein. The output data source 14 is the resulting data source whose attributes and tuples correspond to the anonymity level specified by the data holder. According to other embodiments, as described further herein, the user(s) may specify other inputs to the system 10.

According to one embodiment, before any output data source 14 is generated, the deidentification module 16 may tag each attribute of the input data source 12 as either requiring an equivalence class substitution or a generalization when its associated values are to be released. If values of an attribute tagged as using equivalence class substitution are to be released, the deidentification module 16 may use arbitrary replacement values of the attribute in the released data. The Social Security number (SSN) attribute in FIG. 5 provides an example of an equivalence class substitution. A strong one-way hashing (encryption) algorithm may be used to determine the replacement value.

Alternatively, if an attribute is tagged as requiring a generalization replacement, then an accompanying generalization hierarchy may be assigned to the attribute. The deidentification module 16 may iteratively compute increasingly less specific versions of values for the attribute until eventually the desired anonymity level is attained. For example, a birthdate attribute may first have the full month, day and year for each value. If further generalization is necessary, only the month and year may be used. Still further generalization may require that only the year be used, and so on, as the values get less and less specific, moving up the generalization hierarchy. The iterative process may end when there exist k tuples having the same values assigned across a group of attributes (or "quasi-identifier"). This is termed a k requirement based on the anonymity level specified by the end-user and/or data holder, and provides the basis for k-anonymity. In FIG. 5, the quasi-identifier under consideration, because of the size of the data table shown, is only {Race, Birth, Sex, ZIP} and k=2. Therefore, in the output data source 14, there are at least two tuples for each combination of {Race, Birth, Sex, ZIP} released.

According to one embodiment, the data holder (i.e., user) may declare specific attributes and tuples in the input data source 12 as being eligible for release. The data holder may also group a subset of the released attributes into one or more quasi-identifiers and assign a number, such as between 0 and 1, to each attribute eligible for release that identifies the likelihood each attribute within a quasi-identifier will used for linking. A "0" value may mean not likely to be used for linking and a value of "1" may mean a high probability of linking. Such a list is sometimes referred to herein as a "profile." According to another embodiment, the recipient profile need not be specified, in which case the deidentification module 16 may treat all the values as equally sensitive for linking.

The data holder may also specify a minimal overall anonymity level that computes to a value of k. According to another embodiment, rather than specifying the anonymity level, the data holder may specify the value for k. The data holder may also specify a threshold (referred to as "loss" herein) that determines the maximum number of tuples that can be suppressed in the output data source 14, where loss may correspond to at least k tuples. As used herein, the term "anonymity requirement" is used to generally refer to the specified anonymity level or the k value.

The deidentification module 16 may then produce the output data source 14 from the eligible attributes and tuples of the input data source 12 such that each value of a quasi-identifier in the output data source 14 appears in at least k tuples. The k requirement may be accomplished by generalizing attributes within a quasi-identifier as needed and suppressing no more than loss tuples.

In the example of FIG. 5, the record containing the "Asian" entry was removed; the Social Security numbers were replaced with arbitrary (made-up) alternatives; birth dates were generalized to the year; and ZIP codes were generalized to the first three digits.

The overall anonymity level may be a number between 0 and 1 that relates to the minimum k for each quasi-identifier. For such an embodiment, an anonymity level of 0 may provide the original data and a level of 1 forces the deidentification module 16 to produce the most general data possible given the profile of the recipient. All other values of the overall anonymity level between 0 and 1 may determine the operational value of k. The data holder may map the anonymity level to particular values of k based on, for example, analysis of the data in the input data source 12. Information within each attribute may be generalized as needed to attain the minimum k, and "outliers," which are extreme values not typical of the rest of the data, may be removed. Upon examination of the resulting data, every value assigned to each quasi-identifier may occur at least k times with the exception of one-to-one replacement values, as in the case with an equivalence class substitution.

In addition to an overall anonymity level, the data holder may also provide a profile of the needs of the recipient of the data by, for example, specifying for each attribute that is to be released whether the recipient could have or would use information external to the data source that includes data within that attribute. That is, the data holder may estimate on which attributes the recipient might link outside knowledge. Thus, each attribute may have associated with it a profile value between 0 and 1, where 0 represents full trust of the recipient or no concern over the sensitivity of the information within the attribute, and 1 represents full distrust of the recipient or maximum concern of the sensitivity of the attribute's contents. Semantically related attributes that are sensitive to linking, with the exception of one-to-one replacement attributes, may be treated as a single concatenated attribute (a quasi-identifier) that must meet the minimum k requirement, thereby thwarting linking attempts that use combinations of attributes. The role of these profiles may be to help select which attribute within the quasi-identifier will be selected for generalization. If all attributes in the quasi-identifier have the same value, then the attribute having the greatest number of distinct values may be generalized.

According to one embodiment, the data holder may identify the fields which make up the quasi-identifier and the value for k, as discussed previously. According to another embodiment, the data holder may specify either a "0" or a "1" for each sensitive field, and the recipient may specify a "0" or a "1" for the desired level of distortion in the resulting data source 14. The deidentification module 16 may compute the value for k based on these inputs, as described preciously. According to another embodiment, the data holder and/or recipient may specify values between "0" and "1", inclusive.

The deidentification module 16 may provide the most general data that are acceptably specific to the recipient's specification. Because the profile values may be set independently for each attribute, particular attributes that are important to the recipient can result in less generalization from other requested attributes in an attempt to maintain the usefulness of the data. A profile for data being released for public use, however, may be one for all sensitive attributes to ensure maximum protection. The purpose of the profiles are to quantify the specificity required in each attribute (to maintain usefulness) and to identify attributes that are candidates for linking; and in so doing, the profiles may identify the associated risk to patient confidentiality for each release of the data.

Figure 6:
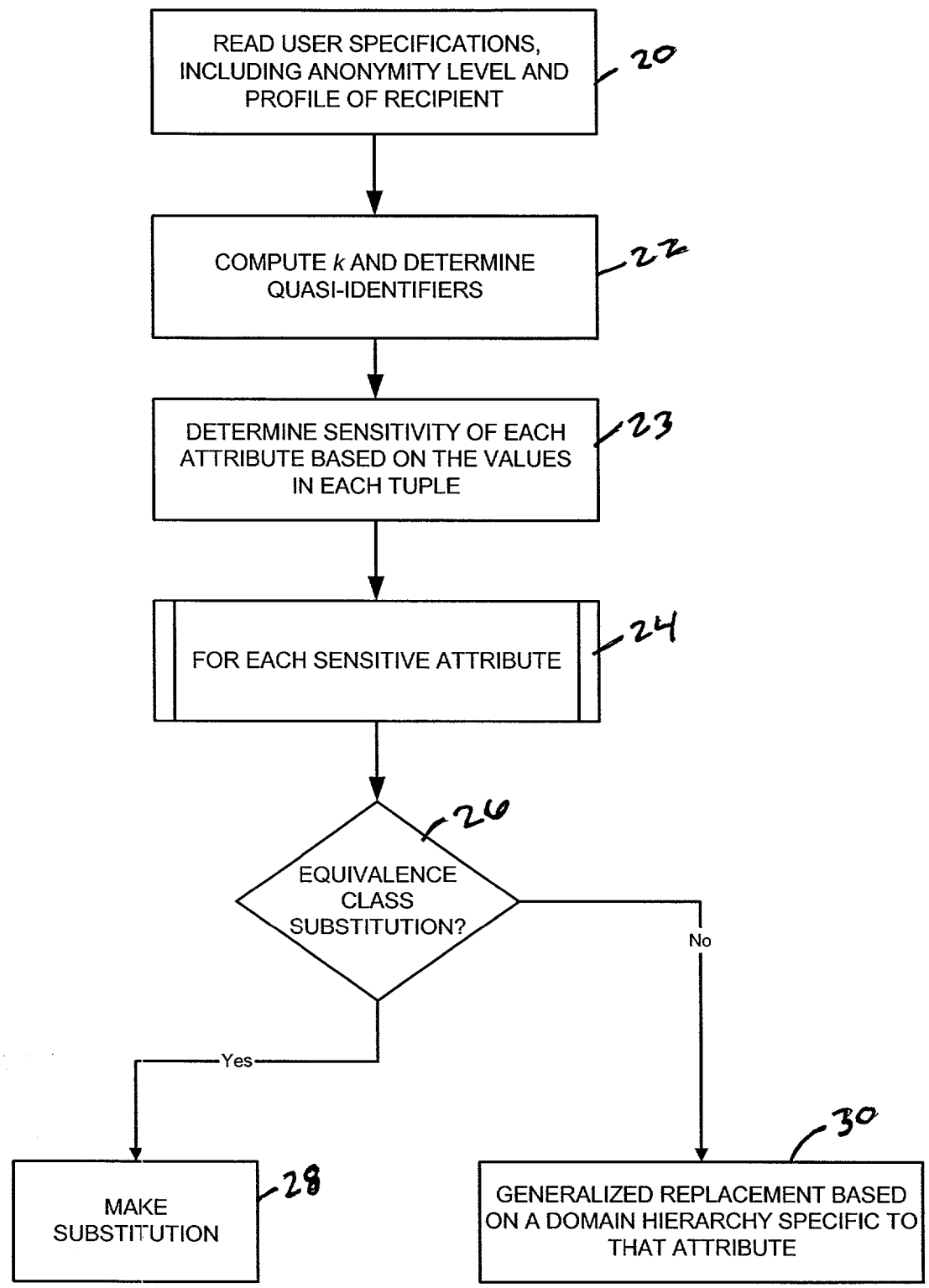
FIG. 6 is a flowchart illustrating the process flow through the deidentification module according to one embodiment of the present invention.
Figure 13A:
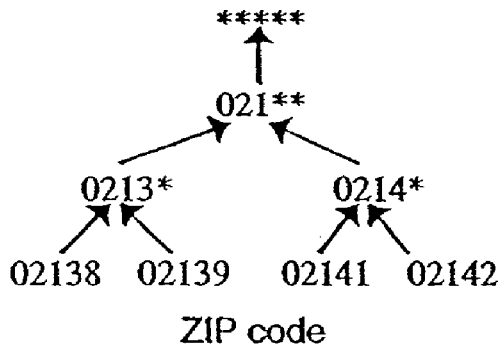
FIGS. 13*a-d* illustrate domain generalization hierarchies for the example provided by FIGS. 12 and 14-16 according to one embodiment of the present invention.
Figure 13B:
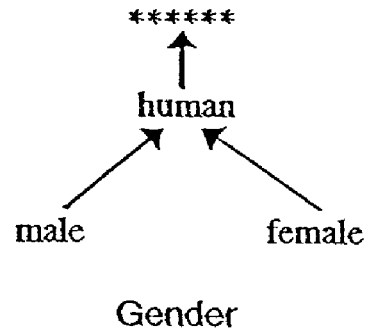
Figure 13C:
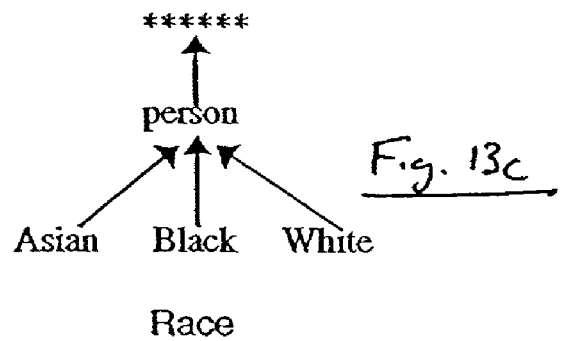
Figure 13D:
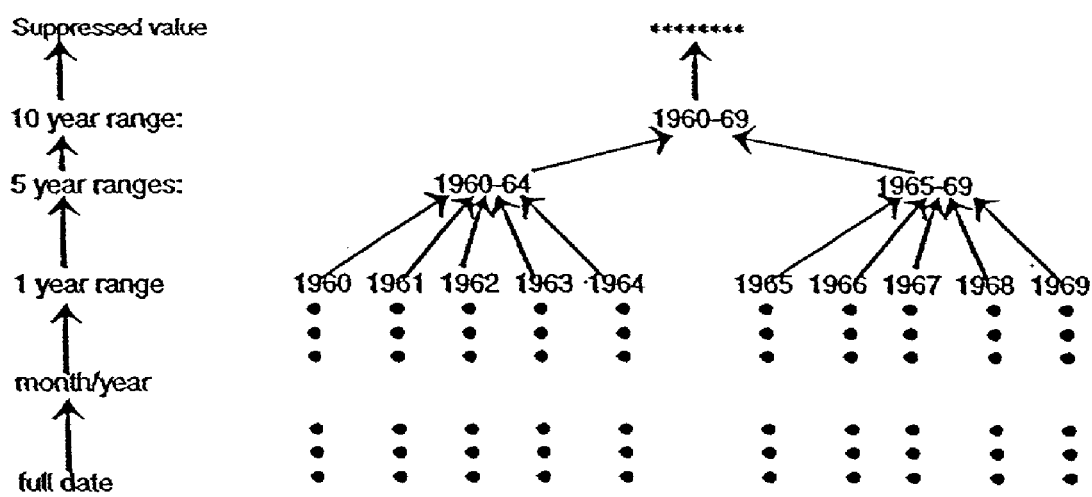

FIG. 6 is a flowchart illustrating an overview of how the deidentification module 16 may function according to one embodiment of the present invention. The process initiates at block 20 where the deidentification module 16 receives the user specifications, which may include, as discussed previously with respect to one embodiment, the anonymity level and the profile of the recipient. The user (or data holder) may specify these inputs via a user-interface, for example. The anonymity level may be, for example, a value between 0 and 1, and the profile of the recipient may be provided by a linking likelihood ($P_f$) for each attribute that may also be a value between 0 and 1. Based on these inputs, at block 22 the deidentification module 16 may compute k and determine the quasi-identifiers in the information to be released. For example, subsets of attributes where $P_f=1$ may be treated as one concatenated attribute (or quasi-identifier), which must satisfy the k-anonymity requirement. As discussed previously, according to other embodiments, the deidentification module 16 may allow the data holder to specify the value for k and/or the quasi-identifier.

At block 23, the deidentification module 16 may determine the sensitivity of each attribute based on the values in each type. Next, at block 24, for each sensitive attribute of the released information, the deidentification module 16 may determine the replacement strategy. According to one embodiment, the first step in this process, at block 26, may be to determine whether the attribute requires an equivalence class substitution. If so, the process advances to block 28, where the deidentification module 16 may make the substitution. According to one embodiment, a strong one-way hashing (encryption) algorithm may be used to generate the replacement value. On the other hand, if an equivalence class substitution is not warranted at block 26, the process may advance to block 30, where the deidentification module 16 may provide a generalized replacement for the attribute based on a domain hierarchy specific to that attribute, as described previously. Thereafter, the output data source 14 may be published. According to one embodiment, the deidentification module 16 may employ a special facility for cases involving multiple tuples attributable to the same person because the number of occurrences and other information contained in the tuples, such as relative dates, can combine to reveal sensitive information. According to such an embodiment, the deidentification module 16 may, for example, transform the data into another data table that makes each row correspond to one person.

FIG. 7 lists the core algorithm of the deidentification module 16 according to one embodiment of the present invention. The inputs to the deidentification module 16 are listed in FIG. 7. The input data source 12 is referred to as "Private Table PT." The output of the method is the output data source 14, referred to as "MGT," which is a generalization of PT[QI] that enforces k-anonymity, where QI is a quasi-identifier. Steps 1 through 3 construct a frequency list containing unique sequences of values across the quasi-identifier in PT along with the number of occurrences of each sequence. The frequency list, "freq," stores the result. Steps 4 through 7 generate a solution by generalizing the attribute with the most number of distinct values and suppressing no more than the allowed number of tuples. Therefore, each tuple in freq is unique and |freq|≦|PT|.

The generalize( ) method of sub-step 6.1 of FIG. 7 is listed in FIG. 8 according to one embodiment. It may use a heuristic to guide its generalization strategy. According to one embodiment, the attribute having the most number of distinct values in the tuples stored in freq is selected and the algorithm may then generalize those values in freq. All the values associated with that attribute are generalized, enforcing generalization at the attribute level.

Step 7 of FIG. 7 assumes that the number of tuples to suppress is less than or equal to loss *|PT|. That is, the frequencies associated with the tuples in freq that are less than k, together total no more than loss *|PT|. An embodiment of the suppress( ) routine of sub-step 7.1 of FIG. 7 is provided at FIG. 9. The routine may traverse through the tuples of freq replacing the tuples whose frequencies are less than k with suppressed values for all the attributes of those tuples, thereby suppressing those tuples. Suppression may be enforced at the tuple-level. Complementary suppression may be performed so that the number of suppressed tuples adheres to the k requirement. An embodiment of the reconstruct( ) routine of sub-step 7.2 of FIG. 7 is provided at FIG. 10. This routine may produce a table, which becomes MGT, based on freq. According to one embodiment, the values stored for each tuple in freq appear in MGT as they do in freq and are replicated in MGT based on the stored frequency. Therefore, |PT|=|MGT|.

FIG. 11 provides the vectoradd( ) routine referred to in sub-steps 5.2, 5.3 and 5.4 of FIG. 8 according to one embodiment. This route may add the tuples associated with (t,occurs,sid) to V to avoid duplication.

According to another embodiment, the method of FIG. 7 may be extended to have the generalized table include attributes not in the quasi-identifier. This may be done, for example, by assigning a unique identifier to each tuple in PT and then storing along with each tuple in freq, the unique identifiers of the corresponding tuples in PT. The unique identifiers may be stored in freq but are not modified or included in step 1 through step 7.1 of FIG. 7. The reconstruct( ) method of sub-step 7.2 (see FIG. 10), however, may be modified to link each tuple from freq to corresponding tuples in PT using the unique identifiers and thereby expand the tuples stored in T to include the additional unchanged attributes of PT that do not belong to QI.

An example of how the deidentification module 16 may operate is described in connection with the input data source (PT) 12 shown in FIG. 12. Unique labels t1 through t12 are used to indicate each tuple for the purpose of this example. Given PT and the domain generalization hierarchies based on the depictions shown in FIGS. 13*a-d*, the deidentification module 16 outputs the output data source (MGT) 14 shown in FIG. 14, as a generalization of PT over the quasi-identifier QI={Race,Birthdate, Gender, ZIP} with no more than loss=k/|PT|, which is 2/12 (or 17%) of the tuples PT suppressed. MGT adheres to a k-anonymity requirement of k=2.

FIG. 15 shows the content of freq after step 3 of the method of FIG. 7, before any generalization is performed. The sequences of values, considered as a unit across QI in freq, are each unique. The numbers appearing below each column in the tabular view of the attributes of QI in freq report the number of distinct values found in each attribute of QI in freq. For example, there are two distinct values, namely "black" and "white" associated with the attribute Race. There are twelve distinct values associated in Birthdate. There are two distinct values for Gender and here are three distinct values for ZIP.

In FIG. 15, the Birthdate attribute has the largest number of distinct values (12) of any attribute of QI in freq. Therefore, at sub-step 6.1, the generalize( ) method recodes those values to month and year of birth in accordance with the domain generalization hierarchy associated with Birthdate shown in FIG. 13*d*. On the second iteration of steps 4 through 6, the Birthdate attribute again has the largest number of distinct values (12) of any attribute of QI in freq. So again, these values are recoded. This time values associated with Birthdate report only the year of birth, as shown in FIG. 16. The two tuples identified as t7 and t8 in FIG. 16 do not occur k times (only once each). In order for this generalization to be a solution, these two tuples in freq would have to be suppressed. That would be 2/12 (or 17%) of the tuples in PT, which is in accordance with the allowable loss of tuples due to suppression (based on loss). Therefore, a solution is found, as shown in FIG. 14.

For the embodiment of the process flow for the deidentification module 16 outlined in FIGS. 7-11, in a worst case scenario, where |freq|=|PT| on the first iteration, step 5 of FIG. 7 executes |PT| times on the first iteration and fractions of |PT| on subsequent iterations. The construction of a frequency list requires visiting each element of the frequency list and, if changes are made due to generalization, the element is removed and then the modified element is added. According to another embodiment, all elements in the frequency list may be compared to the element that is to be inserted.

The embodiment for the deidentification module 16 described previously in connection with FIGS. 7-11, while satisfying the k-anonymity requirement, does not necessarily provide minimally generalized solutions or minimally distorted solutions. This is because the process of FIG. 7 generalizes all values associated with an attribute or suppresses all values within a tuple. In addition, the process of FIG. 7 uses a heuristic, as described previously, to guide the selection of which attribute to generalize. This can lead to unnecessary generalization. Any attribute that is not in the domain of its maximal element could be selected for generalization, though some choices may be better than others.

According to another embodiment, the deidentification module 16 may be configured to use generalization and suppression to find optimal solutions such that data are minimally distorted while still being adequately protected. According to one embodiment, this may be achieved by, for example, dividing data into groups such that the size of each group consists of k or more of the "closest" tuples. In this case, according to one embodiment, closeness may be based on a minimal distance measure derived from distance vectors.

According to such an embodiment, the deidentification module 16 may provide a solution to finding similarity matches in a high dimensional space with data consisting of primarily categorical values. The approach may be based on combining generalization and suppression, and on using the resulting hierarchies as a semantically useful grouping that reflects a partial ordering on values. By cell generalization, it is meant that a value can be replaced by a less precise but semantically consistent alternative. Cell suppression in this context may be considered the most general value possible because semantically no information is released. The distance between two values may then be measured in terms of the minimal level up the generalization hierarchy at which the two values have a common ancestor. This precision metric provides the basis for a semantically meaningful measure of distance. Given an input data source 12 and a value for k, the deidentification module 16 for such an embodiment may group the tuples of the table in as many clusters as necessary such that each cluster contains at least k of its closest tuples. In terms of anonymity, having k tuples that are indistinguishable is the basis for k-anonymity protection. The process flow through the deidentification module 16 according to such an embodiment may be similar to that of FIG. 6, except that the deidentification module 16 uses the quasi-identifier(s) and the k-anonymity requirement that is to be enforced on the quasi-identifier(s) to find optimal solutions such that data are minimally distorted while still being adequately protected.

Figure 17:
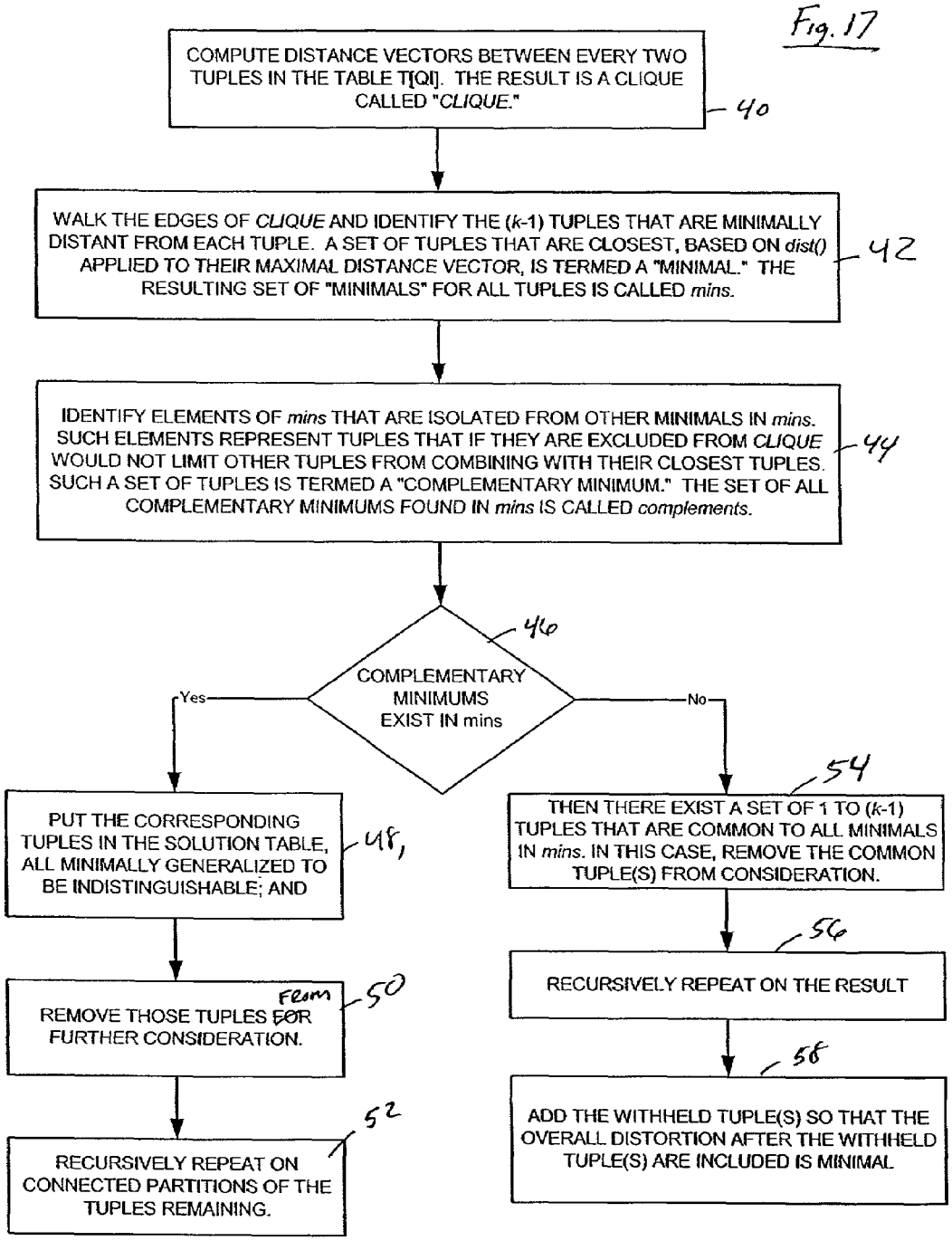
FIG. 17 is a diagram of the process flow through the deidentification module according to another embodiment.

FIG. 17 is a diagram of the process flow through the deidentification module 16 for finding optimal solutions such that data are minimally distorted while still being adequately protected, according to one embodiment. The process initiates at block 40, where the deidentification module 16 may test for some base conditions. These conditions include that: (1) if the number of tuples in the table is zero, then an empty table is returned; (2) if the number of tuples in the table is less than k, an error results; and (3) if the number of tuples in the table is greater than or equal to k, but less than 2 k, all the tuples are generalized into one cluster that is returned as the solution. In all the cases, the deidentification module 16 may continue by automatically computing distance vectors between every two tuples and organizing the result in a clique. Each distance vector recorded on an edge of the clique reports the generalization needed in order for the two incident tuples to have the same generalized result.

Next the process advances to block 42, where the deidentification module walks the edges of the clique to identify groups of k tuples that are "closest" in terms of distance vectors. A set of k tuples that are minimally distant denote a possible cluster of tuples in the generalized solution. Each of the tuples in the cluster appears in the generalized solution with the same generalized values. The set of all k-sized clusters determined to minimally include a couple is called mins. Each cluster is called a "minimal." The remainder of the process works with mins and subsets and partitions of mins to identify which group of clusters in mins best accounts for all the tuples that when generalized in accordance with their designated clusters would yield minimal distortion in the overall generalized solution.

Some of the clusters in mins may consist of tuples that if their attributes were generalized to the same values would not limit the ability of other tuples to combine with their closest tuples. Such a cluster may be termed a "complementary minimum." At block 44, the deidentification module 16 traverses through mins identifying any complementary minimums.

At block 46, the deidentification module 16 determines whether complementary minimums exist in mins. If complementary minimums do exist, then the process advances to block 48, where the deidentification module 16 puts the corresponding tuples in the solution table, all minimally generalized to be indistinguishable. Next, at block 50, the deidentification module removes those tuples from further consideration. At block 52, the process may be repeated on connected partitions of the tuples remaining. By this process, the tuples that comprise a complementary minimum are generalized together and added to the generalized solution. Recall, a cluster in mins, from block 42, identified its constituent tuples as being minimally distant and the cluster as containing k tuples. Therefore, if the cluster is a complementary minimum, it provides a solution for its constituent tuples. Clusters remaining in mins, after complementary minimums are removed, have groups of clusters that share tuples.

Returning to block 46, if there do not exist any complementary minimums in mins, this is a special situation in which groups of clusters share one or more common tuples. The process advances to block 54 where the common tuple(s) are removed from consideration. At block 56, the process is recursively repeated on the result, and at block 58 the withheld tuple(s) are added so that the overall distortion after the withheld tuple(s) are included is minimal.

FIG. 18 lists the core algorithm for the deidentification module 16 in more detail according to one embodiment. For purposes of identification, this algorithm is referred to as "k-Similar" in FIG. 18. The inputs to the deidentification module 16 are listed in FIG. 18. These inputs include the input data source 12, referred to as "Table T," a quasi-identifier QI=$(A_1, \ldots, A_n)$, a k-anonymity constraint k, and domain and value generalization hierarchies $DGH_{Ai}$ and $VGH_{Ai}$, where i=1, . . . ,n with accompanying functions $f_{Ai}$. The output of the deidentification module 16 (ie., the output data source 14) is a k-minimal distortion of T[QI]. The routine provided in FIG. 18 begins at step 1 by expanding T to include an attribute labeled ID whose values serve as a unique identifier (or key) of each tuple in T. From this point forward, the deidentification module 16 may have the ability to uniquely refer to a tuple in T by using its associated value of ID.

Step 2 of the k-Similar algorithm, provided in FIG. 18, produces a clique of the tuples of T stored in a 2-dimensional array named "clique." The method CliqueConstruct( ), an embodiment of which is provided at FIG. 19, performs the construction according to one embodiment. Each node in the clique is a tuple. Each edge records the distance vector that corresponds to the distance between the tuples whose nodes are incident. The method Distance( ), an embodiment of which is provided at FIG. 20, computes the distance vector between two tuples using the value generalization hierarchies $VGH_{Ai}$, where i=1, . . . , n with accompanying functions $f_{Ai}$. The distance vector records the minimal generalization strategy needed for the two tuples to have the same and generalized values.

Returning to FIG. 18, at step 3 the deidentification module 16 may execute the method kSimilarRun( ), an embodiment of which is provided at FIG. 21 and which will be described in more detail hereinafter. The kSimilarRun( ) method of FIG. 21 returns a set of clusters that minimally generalizes the tuples of each cluster together so that they become indistinguishable results in a table that is a k-minimal distortion of T[QI]. The method TableConstruct( ), an embodiment of which is provided at FIG. 22, takes the set of clusters from kSimilarRun( ), generalizes the tuples of each cluster, and then returns the generalized table. Each cluster therefore identifies a group of tuples that in the solution set are indistinguishable across QI. Therefore, the k-Similar approach can be described as translating the problem into one of partitioning tuples. This may be done by the kSimilarRun( ) routine, provided at FIG. 21.

The kSimilarRun( ) routine may begin by testing for the base conditions in steps 1 through 3. These conditions may be based on the size of the table provided to kSimilarRun. At step 1, if the number of tuples in the table is zero, an empty set of clusters is returned denoting the empty table. At step 2, if the number of tuples is less than k, an error results because the k requirement cannot be satisfied on a table having less than k tuples. At step 3, if the number of tuples in the table is greater than or equal to k, but less than 2 k, all the tuples are generalized into one cluster designating that all the tuples of the table are to be generalized together.

At step 4 of the kSimilarRun( ) method, the deidentification module 16 walks the edges of clique using the method GenerateMinimums( ), an embodiment of which is provided at FIG. 23, to identify groups of k tuples that are "closest" in terms of distance vectors. The method traverse( ), an embodiment of which is provided in FIG. 24, may perform the actual transversal on clique given a particular starting tuple t. The method traverse( ) returns the cluster(s) of size k containing t and t's closest tuples that when combined have less distortion than any other combination of k tuples that include t. The method GenerateMinimums( ) may execute traverse( ) on each tuple. The end result is a set of all k-sized clusters determined to minimally include a tuple. It may be called mins. Each cluster in mins may be called a "minimal." As described hereinafter, the remainder of the deidentification module 16 may work with mins and partitions of mins to identify which group of clusters in mins best accounts for all the tuples that when generalized in accordance to their designated clusters would yield minimum distortion in the overall generalized solution.

Some of the clusters in mins may consist of tuples that if their attributes were generalized to the same values would not limit the ability of other tuples to combine with their closest tuples. Such a cluster may be termed a "complementary minimum." Step 5 of the kSimilarRun( )method, provided at FIG. 21, executes the FindComplements( ) routine, an embodiment of which is provided at FIG. 25, to identify complementary minimums within mins. Such clusters can be partitioned as an independent sub-solution. The resulting set of complementary minimums found may be called complements.

The sub-steps of step 6 of the kSimilarRun( )method (see FIG. 21) execute only if complementary minimums are found in mins. In that case, complements returns as part of the solution and kSimilarRunParts( ), an embodiment of which is provided at FIG. 26, executes on the remaining tuples and minimals to recursively apply the algorithm on partitions of connected clusters. If no complementary minimums are found then complements has no elements, and so in step 7, kSimilarRunParts( ) (see FIG. 26) may execute on all the tuples and minimals under consideration.

The method kSimilarRunParts( ) may employ mutual recursion by executing kSimilarRun( ) on each connected partition of the remaining clusters in mins. The method Partition( ), an embodiment of which is listed at FIG. 27, may be used in step 2 of kSimilarRunParts( ) to identify connected clusters within the given mins. If the returned partition has less than 2 k elements, then in step 3.1, kSimilarRun( ) may be used to combine the tuples of that partition into a single cluster as part of the overall solution.

If the returned partition, identified as $T_1$, has 2 k or more elements, then the partition has a special configuration in which all minimals within the partition share one or more common tuples. This situation may be handled in step 4 of kSimilarRunParts( ) (see FIG. 26). At step 4.1, the method kSimilarRunParts( ) may deploy the method CommonTuples( ), an embodiment of which is listed at FIG. 28, to identify the set of 1 to (k−1) tuples that appear within each cluster of the partition. These tuples may be stored in a set called withheld. If the number of tuples in the partition, not including the tuples withheld, is less than 2 k, then the method addTuple( ), an embodiment of which is listed at FIG. 29, may execute to determine which clusters in the partition should include the withheld tuples. The decision may be made so that the overall result has minimal distortion. On the other hand, if the number of tuples in the partition, not including the tuples withheld, is greater than or equal to 2 k, then kSimilarRun may be executed using mutual recursion on the partition not including the withheld tuples. The method addTuple (see FIG. 29) may then execute afterwards to determine which cluster(s) in the result will include the withheld tuples.

As previously stated, the final step of the k-Similar algorithm of FIG. 18 uses TableConstruct( ), an embodiment of which is provided at FIG. 22, to construct a generalized table from the resulting set of clusters from kSimilarRun( ). It can be shown that the final table resulting from the k-Similar algorithm is a k-minimal distortion of the original table using cell-level generalization and suppression.

Figures 30, 31, 32, 33:
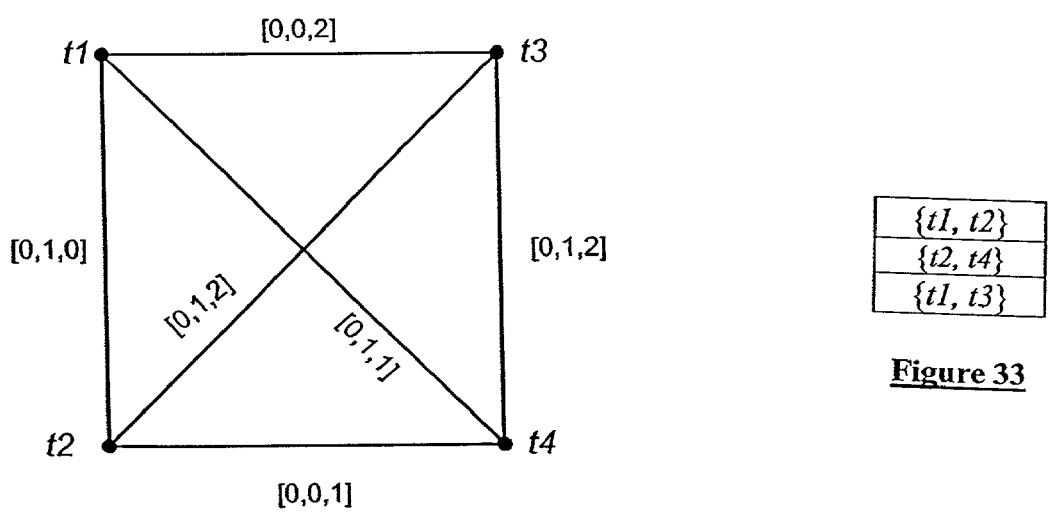
FIGS. 30-33 illustrate an example of how the deidentification module operates according to another embodiment of the present invention.

An example of how the deidentification module 16 operates according to one embodiment using the algorithms of FIGS. 18-29 is provided in conjunction with FIGS. 30-33 Given the private table PT (i.e., input data source 12) shown in FIG. 30, the domain and value generalization hierarchies (DGH and VGH) based on FIG. 13, and a k-anonymity requirement of k=2, the deidentification module 16, employing the algorithms of FIGS. 18-29 according to such an embodiment, yields the table GT (i.e., output data source 14) shown in FIG. 31 as a k-minimal distortion of the input data source 12 (PT) over the quasi-identifier QI={HomeZIP, HospZIP, WorkZIP}. The following discussion describes how that result is reached.

The table of FIG. 30 shows the uniquely identifying values t1, t2, t3 and t4 appended to the table after step 1 of the k-similar algorithm of FIG. 18 executes. These values are associated with the ID attribute. FIG. 32 shows clique, which is constructed after step 2 of the algorithm of FIG. 18 concludes. The nodes of the clique correspond to the tuples of PT. The edges are labeled with the distance vectors between every two tuples in PT.

None of the base conditions in first 3 steps of kSimilarRun( ) are applicable in this example. T in this case is PT. It has 4 tuples and k=2, so |T|=2 k. FIG. 33 shows the value of mins after step 4 of the routine of FIG. 18 concludes. The method GenerateMinimumns( ) identifies the set of minimals for each tuple by traversing clique to identify each tuple's nearest (k−1) tuples. Traversing clique from t1 provides the minimal {t1, t2}, from t2 provides the minimals {t1, t2} and {t2, t4}, from t3 provides the minimal {t1, t3}, and from t minimal {t2, t4}.

The minimals {t1, t3} and {t2, t4} are returned as complementary minimums by FindComplements( ) (see FIG. 25). Therefore, complements={{t1, t3}, {t2, t4}} after step 5 of kSimilarRun( ). When step 6 of kSimilarRun( ) concludes, T is empty. Therefore, complements is returned at step 7 of kSimilarRun( ) as the set of clusters that are minimally distorting. The call to kSimilarRunParts( ) in step 7 of kSimilarRun( ) return Ø because T is empty. The final step of kSimilarRun( ) executes TableConstruct( ) on clusts={{t1, t3}, {t2, t4}}, the result of which is shown in FIG. 31 with the ID values still appended for ease of reference.

The possible cluster combinations and their distortion are: {{t1, t2}, {t3, t4}} at 8 levels of generalization is 2.67; {{t1, t3}, {t2, t4}} at 6 levels of generalization is 2.00; and {{t1 t4}, {t2, t3}} at 10 levels of generalization is 3.33. The combinatio distortion is {{t1, t3}, {t2, t4}}, which is the same found by the algorithm of FIG. 18.

Although the present invention has been described herein with respect to certain embodiments, those of ordinary skill in the art will recognize that many modifications and variations of the present invention may be implemented. For example, certain steps of some of the methods presented herein may be performed in different orders. The foregoing description and the following claims are intended to cover all such modifications and variations.

What is claimed is:

1. A system for deidentifying entries in an input data source having field-structured data organized in fields and entries, comprising:

a processor; and a deidentification module comprising software code which when executed by the processor causes the procecessor to anonymize entries in a version of the input data source by generalizing at least one entry value of the version of the input data source to yield an output data source having field-structured data organized in fields and entries, wherein the generalization is such that a value of each entry within at least one field of the output data source occurs at least k times, and wherein a value of k is such that entries of the output data source match a specified anonymity requirement, and wherein the processor, when executing the software code of the deidentification module, anonymizes entries in the version of the input data source by at least one of suppressing or replacing entry values in the version of the input data source such that the entries of the output data source match the specified anonymity requirement.

2. The system of claim 1, wherein the deidentification module is further for causing the processor to:

receive a recipient profile; and anonymize entries in the version of the input data such that entries of the output data source match the specified anonymity requirement with respect to the recipient profile.

3. The system of claim 2, wherein the recipient profile identifies a likelihood that entries in the output data source will be useful for linking with another data source.

4. The system of claim 1, wherein the deidentification module is for causing the processor to anonymize entries in the version of the input data source such that the entries in the output data source are minimally distorted.

5. The system of claim 1, wherein the version of the input data source includes a copy of the input data source.

6. A system for deidentifying entries in an input data source having field-structured data organized in fields and entries, comprising:

a processor; and a deidentification module comprising software code which when executed by the processor causes the the processor to anonymize entries in a version of the input data source by generalizing at least one entry value of the version of the input data source to yield an output data source having field-structured data organized in fields and entries, wherein the generalization is such that a value of each entry within at least one field of the output data source occurs at least k times, and wherein a value of k is such that entries of the output data source match a specified anonymity requirement, wherein the processor, when executing the software code of the deidentification module, anonymizes entries in the version of the input data source by:

determining whether each field in the version of the input data source requires one of an equivalent class substitution or a generalization; and replacing an entry value in a field of each entry with a replacement value determined according to a generalization hierarchy when a determination is made that the field requires a generalization.

7. The system of claim 6, wherein the deidentification module is further for causing the processor to replace an entry value in a field in each entry with a replacement value determined according to a strong one-way hashing algorithm when a determination is made that the field requires an equivalent class substitution.

8. The system of claim 6, wherein the deidentification module is further for causing the processor to replace an entry value in a field in each entry with a replacement value determined according to a generalization hierarchy when a determination is made that the field requires a generalization by iteratively computing increasingly less specific values for each field until the specified anonymity requirement is obtained.

9. The system of claim 8, wherein the deidentification module is further for causing the processor to iteratively compute increasingly less specific values for each field until the specified anonymity requirement is obtained by iteratively computing less specific values for each field until there exists a number of entries corresponding to the specified anonymity requirement having the same values across a group of fields.

10. A computer readable medium, having stored thereon instructions, which when executed by a processor, cause the processor to:

read a specified anonymity requirement;

anonymize entries in a version of an input data source, the input data source having field-structured data organized in fields and entries, by generalizing at least one entry value of the version of the input data source to yield an output data source having field-structured data organized in fields and entries, wherein the generalization is such that a value of each entry within at least one field of the output data source occurs at Least k times, and wherein a value of k is such that entries of the output data source match the specified anonymity requirement;

determine whether each field in the version of the input data source requires one of an equivalent class substitution or a generalization; and replace an entry value in a field of each entry with a replacement value determined according to a generalization hierarchy when a determination is made that the field requires a generalization.

11. The computer readable medium of claim 10, having further stored thereon instructions, which when executed by the processor, cause the processor to:
  read a specified recipient profile; and
  anonymize entries in the version of the input data source to match the specified anonymity requirement with respect to the recipient profile.

12. The computer readable medium of claim 11, wherein the recipient profile identifies a likelihood that entries in the output data source will be useful for linking with another data source.

13. The computer readable medium of claim 10, having further stored thereon instructions, which when executed by the processor, cause the processor to:
  replace an entry value in a field in each entry with a replacement value determined according to a strong one-way hashing algorithm when a determination is made that the field requires an equivalent class substitution.

14. The computer readable medium of claim 10, having further stored thereon instructions, which when executed by the processor, cause the processor to:
  replace an entry value in a field in each entry with a replacement value determined according to a generalization hierarchy when a determination is made that the field requires a generalization by iteratively computing increasingly less specific values for each field until the specified anonymity requirement is obtained.

15. The computer readable medium of claim 14, having further stored thereon instructions, which when executed by the processor, cause the processor to:
  iteratively compute increasingly less specific values for each field until the specified anonymity requirement is obtained by iteratively computing less specific values for each field until there exists a number of entries corresponding to the specified anonymity requirement having the same values across a group of fields.

16. The computer readable medium of claim 10, having further stored thereon instructions, which when executed by the processor, cause the processor to anonymize the entries in the version of the input data source such that the entries in the output data source are minimally distorted.

17. A method for deidentifying entries in an input data source having field-structured data organized in fields arid entries, comprising:
  receiving a specified anonymity requirement; and
  anonymizing entries in a version of the input data source by generalizing at least one entry value of the version of the input data source to yield an output data source, the output data source having field-structured data organized in fields and entries, wherein the generalization is such that a value of each entry within at least one field of the output data source occurs at least k times, and wherein a value of k is such that entries of the output data source match the specified anonymity requirement,
  wherein anonymizing entries in the input data source includes:
    determining whether each field in the version of the input data source requires one of an equivalent class substitution or a generalization; and
    replacing an entry value in a field of each entry with a replacement value determined according to a generalization hierarchy when a determination is made that the field requires a generalization.

18. The method of claim 17, further comprising receiving a specified recipient profile, and wherein anonymizing entries includes anonymizing entries in the version of the input data source such that the entries of the output data source match the specified anonymity requirement with respect to the recipient profile.

19. The method of claim 18, wherein the recipient profile identifies a likelihood that entries in the output data source will be useful for linking with another data source.

20. The method of claim 17, wherein anonymizing entries in the version of the input data source further includes replacing an entry value in a field of each entry with a replacement value determined according to a strong one-way hashing algorithm when a determination is made that the field requires an equivalent class substitution.

21. The method of claim 17, wherein replacing an entry value in a field of each entry with a replacement value determined according to a generalization hierarchy when a determination is made that the field requires a generalization includes iteratively computing increasingly less specific values for each field until the specified anonymity requirement is obtained.

22. The method of claim 21, wherein iteratively computing increasingly less specific values for each field until the specified anonymity requirement is obtained includes iteratively computing less specific values for each field until there exists a number of entries corresponding to the specified anonymity requirement having the same values across a group of fields.

23. The method of claim 17, wherein anonymizing entries in the version of the input data source such that the entries of the output data source match the specified anonymity requirement with respect to the recipient profile includes anonymizing entries in the version of the input data source such that the entries in the output data source are minimally distorted.

24. A system for deidentifying entries in an input data source, having field-structured data organized in fields and entries, comprising:
  means for anonymizing entries in a version of the input data source by generalizing at least one entry value of the version of the input data source to yield an output data source having field-structured data organized in fields and entries, wherein the generalization is such that a value of each entry within at least one field of the output data source occurs at least k times, and wherein a value of k is such that entries of the output data source match a specified anonymity requirement,
  wherein the means for anonymizing entries in the input data source is further for:
    determining whether each field in the version of the input data source requires one of an equivalent class substitution or a generalization; and
    replacing an entry value in a field of each entry with a replacement value determined according to a generalization hierarchy when a determination is made that the field requires a generalization.

25. The system of claim 24, wherein the means for anonymizing further include means for anonymizing entries in the version of the input data source such that the entries of the output data source match the specified anonymity requirement with respect to a recipient profile.

26. The system of claim 25, wherein the recipient profile identifies a likelihood that entries in the output data source will be useful for linking with another data source.

27. The system of claim 24, wherein the means for anonymizing entries is further for replacing an entry value in a field of each entry with a replacement value determined according to a strong one-way hashing algorithm when a determination is made that the field requires an equivalent class substitution.

28. The system of claim 24, wherein the means for anonymizing is further for replacing an entry value in a field of each entry with a replacement value determined according to a generalization hierarchy when a determination is made that the field requires a generalization by iteratively computing increasingly less specific values for each field until the specified anonymity requirement is obtained.

29. The system of claim 28, wherein the means for anonymizing is further for iteratively computing increasingly less specific values for each field until the specified anonymity requirement is obtained by iteratively computing less specific values for each field until there exists a number of entries corresponding to the specified anonymity requirement having the same values across a group of fields.

30. The system of claim 24, wherein the means for anonymizing is further for anonymizing entries in the version of the input data source such that the entries in the output data source are minimally distorted.

* * * * *